(12) United States Patent
Meyer et al.

(10) Patent No.: US 9,943,343 B2
(45) Date of Patent: Apr. 17, 2018

(54) INSTRUMENT AND METHOD FOR REDUCING AND SECURING SPINAL RODS

(71) Applicant: Alphatec Spine, Inc., Carlsbad, CA (US)

(72) Inventors: Nathan Meyer, Vista, CA (US); Anand Parikh, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 15/276,059

(22) Filed: Sep. 26, 2016

(65) Prior Publication Data

US 2017/0007302 A1    Jan. 12, 2017

Related U.S. Application Data

(62) Division of application No. 13/957,218, filed on Aug. 1, 2013, now Pat. No. 9,526,537.

(60) Provisional application No. 61/679,294, filed on Aug. 3, 2012.

(51) Int. Cl.
*A61B 17/88* (2006.01)
*A61B 17/70* (2006.01)

(52) U.S. Cl.
CPC ...... *A61B 17/7085* (2013.01); *A61B 17/7086* (2013.01); *A61B 17/7091* (2013.01)

(58) Field of Classification Search
CPC ................. A61B 17/7085; A61B 17/7086
USPC ....................... 606/99, 86 A, 86 B
See application file for complete search history.

(56) References Cited

U.S. PATENT DOCUMENTS

| | | | |
|---|---|---|---|
| 5,649,931 A | 7/1997 | Bryant et al. | |
| 2001/0053914 A1* | 12/2001 | Landry | A61B 17/1757 606/99 |
| 2004/0220612 A1 | 11/2004 | Swainston et al. | |
| 2006/0111713 A1 | 5/2006 | Jackson | |
| 2006/0247630 A1* | 11/2006 | Iott | A61B 17/701 606/86 A |
| 2008/0077139 A1* | 3/2008 | Landry | A61B 17/1757 606/86 A |
| 2008/0243190 A1 | 10/2008 | Dziedzic et al. | |
| 2009/0105712 A1 | 4/2009 | Dauster et al. | |
| 2009/0171391 A1 | 7/2009 | Hutton et al. | |
| 2011/0034962 A1 | 2/2011 | Dunbar, Jr. et al. | |

* cited by examiner

*Primary Examiner* — Eduardo C Robert
*Assistant Examiner* — Tara R Carter
(74) *Attorney, Agent, or Firm* — Dinsmore & Shohl LLP

(57) ABSTRACT

A method for reducing a fixation rod is provided. The method minimizes the surgical corridor by performing fixation within the surgical corridor defined by the screw extender. The screw extender is attached to the spinal implant. The method includes the steps of coupling the proximal end of a first cannulated body with the screw extender and rotating a second cannulated body within the first cannulated body. The method proceeds to the step of actuating a rod pusher with a first driving feature so as to engage the rod pusher with the fixation rod. The rod pusher includes a bore. The method proceeds to the step of rotating an inserter shaft within first cannulated body, second cannulated body and bore of the rod pusher, the inserter shaft including a proximal end with a second driving feature and a distal end with a setscrew attachment feature.

12 Claims, 14 Drawing Sheets

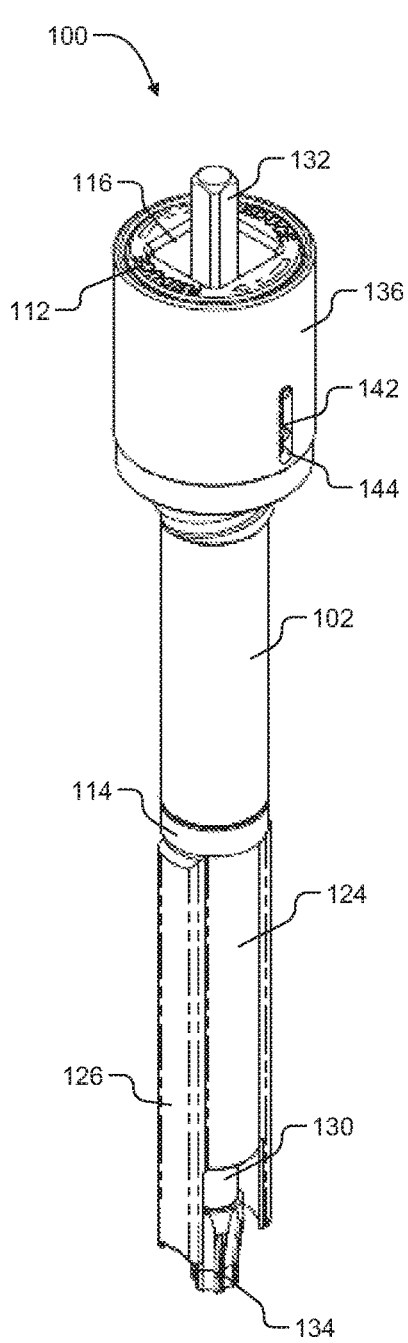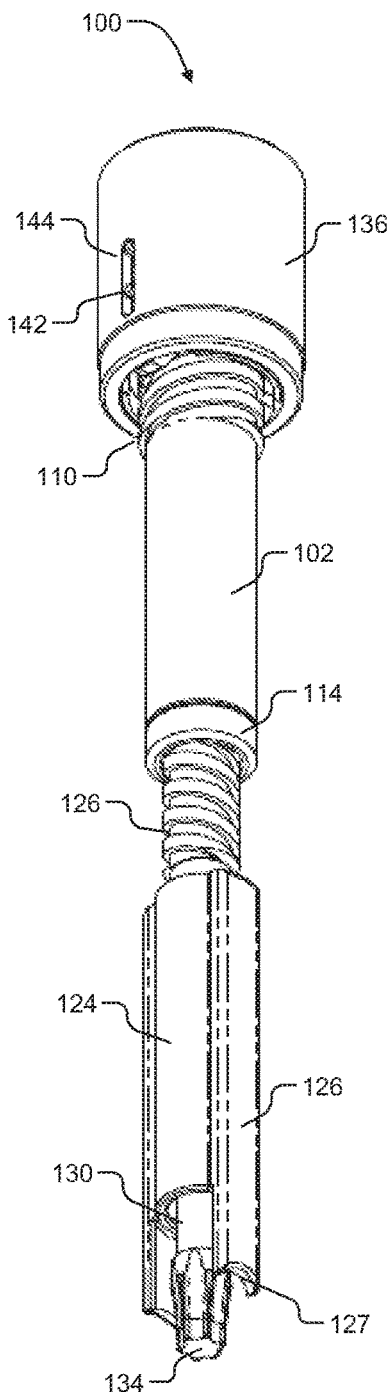
FIG. 1A
FIG. 1B

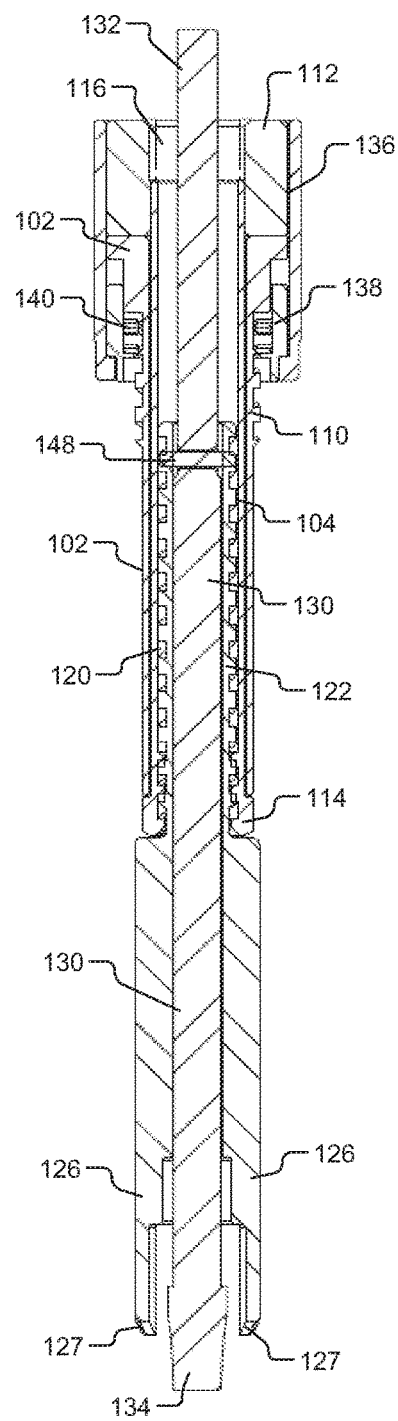
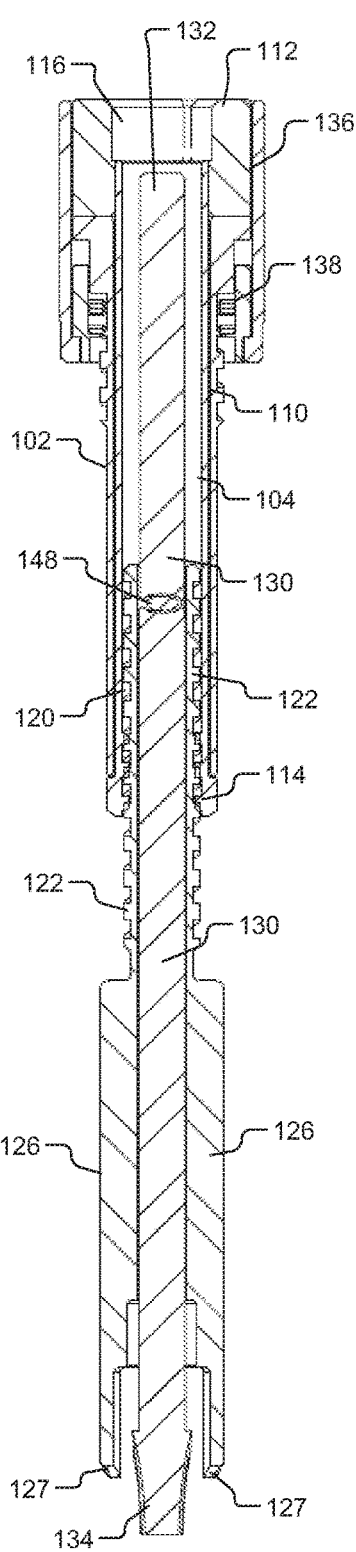
FIG. 7A
FIG. 7B

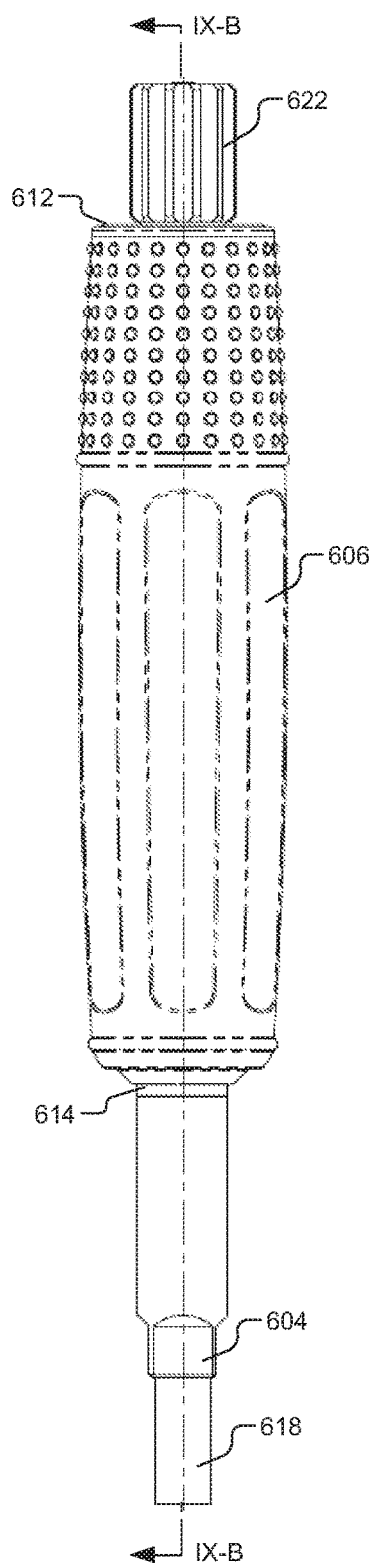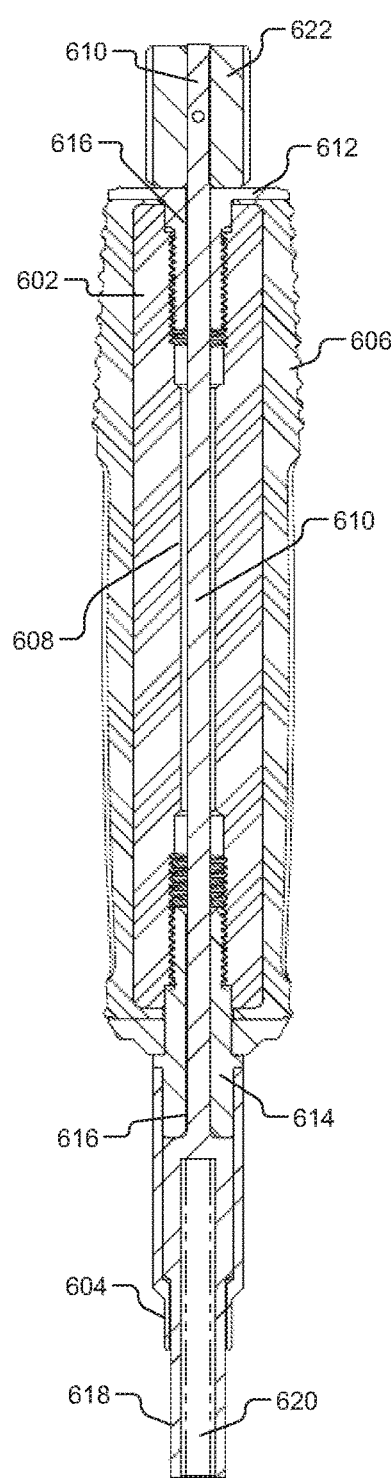
FIG. 9A
FIG. 9B

INSTRUMENT AND METHOD FOR REDUCING AND SECURING SPINAL RODS

CROSS-REFERENCE TO RELATED APPLICATIONS

The present application is a divisional of U.S. application Ser. No. 13/957,218 filed Aug. 1, 2013, which claims priority from U.S. Provisional Application Ser. No. 61/679,294, filed on Aug. 3, 2012 and entitled "MIS Rod Inserter with Set Screw Inserter" which is incorporated herein by reference in its entirety.

FIELD

The present disclosure generally relates to the field of spinal orthopedics, and more particularly to instruments and methods for reducing and securing spinal rods within a spinal fixation system.

BACKGROUND

The spine is a flexible column formed of a plurality of bones called vertebrae separated by cartilaginous disks. The spine includes seven cervical (neck) vertebrae, 12 thoracic (chest) vertebrae, five lumbar (lower back) vertebrae, and the fused vertebrae in the sacrum and coccyx that help to form the hip region. While the shapes of individual vertebrae differ among these regions, each is essentially a short hollow tube containing the bundle of nerves known as the spinal cord. Individual nerves, such as those carrying messages to the arms or legs, enter and exit the spinal cord through gaps between vertebrae. The different vertebrae are connected to one another by means of articular processes and intervertebral, fibrocartilaginous bodies.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. The spine curves in at the lumbar region, back out at the thoracic region, and back in at the cervical region.

Various spinal disorders may cause the spine to become misaligned, curved, and/or twisted or result in fractured and/or compressed vertebrae. It is often necessary to surgically correct these spinal disorders. Spinal fusion is a procedure that promotes fusing or growing together of two or more vertebrae in the spine. Spinal fusion can be performed to straighten a spine deformed by scoliosis, neuromuscular disease, cerebral palsy, or other disorders; prevent further deformation; support a spine weakened by infection or tumor; reduce or prevent pain from pinched or injured nerves; or compensate for injured vertebrae or disks. The procedure may improve posture, increase ability to ventilate the lungs, prevent pain, or treat spinal instability and reduce the risk of nerve damage.

One of the types of spinal fusion procedures is a posterior spinal fusion surgery. This procedure is performed posteriorly, or from the back of patient, as opposed to anteriorly, or through the abdomen. Generally the correct curvature is obtained by manipulating the vertebrae into their proper position and securing that position with a rigid system of screws and rods. The screws may be inserted into the pedicles of the vertebrae to act as bone anchors, and the rods may be inserted into heads of the screws. Two rods may run substantially parallel to the spine and secure the spine in the desired shape and curvature. Thus the rods, which are shaped to mimic the correct spinal curvature, force the spine into proper alignment. Bone grafts are then placed between the vertebrae to aid in fusion of the individual vertebrae together to form a correctly aligned spine.

There have been various approaches and systems for performing posterior spinal surgery. Some conventional systems include titanium construction that is compatible with current CT and MRI scanning technology, low profile implant systems, top-loading and top-tightening systems, and other parameters. Some systems also include cross-connectors that allow a one-piece implant to be applied to a dual-rod construct for a top-loading approach.

In minimally invasive surgery (MIS), access to the screws may be severely limited to the space provided by extenders or extension members attached to the screw heads. For example, an exemplary posterior system including screws and extenders may be found in commonly assigned U.S. Application Pub. No. 2010/0036443, entitled "Systems and Methods for Spinal Fixation" filed on Aug. 11, 2009 to Hutton et al. The system may be used in a MIS setting. The extenders may attach to the screw heads at a distal end and extend outside the MIS surgical opening at a proximal end. The extenders are generally tubular and may also include slots along their lengths for insertion of fixation rods. The extenders include a cannula extending from the proximal end to the distal end for insertion of various instruments and setscrews. For example, one or more instruments may be required to position the fixation rods into the heads of the screws, seat the rods within the heads, insert set screws to retain the rods within the heads, and tighten the set screws to rigidly fix the system together to ensure proper bone fusion.

A typical rod reduction instrument may include a cannulated tube that slides over the screw extender. For example, the reduction instrument may include a cannula through which the screw extender may slide. Thus, the reduction instrument may include a larger footprint than the surgical opening. The larger footprint may increase the size of the surgical opening. The reduction instrument may also inhibit loading and insertion of a setscrew used to secure the rod within the screw head. For example, after reduction of the rod into the screw head, a separate instrument may be used to insert the setscrew and advance the setscrew into the screw head to fix the rod therein.

SUMMARY

An instrument for reducing a fixation rod within a screw extender that attaches to a spinal implant includes first, second, and third cannulated bodies and an inserter shaft. The first cannulated body includes a proximal end that couples with the screw extender. The second cannulated body rotates within the first cannulated body and includes a proximal end with a first driving feature and a distal end with an internal threaded portion. The third cannulated body includes a proximal end that engages the internal threaded portion and a distal end with a rod pusher for engaging the fixation rod. The inserter shaft rotates within the third cannulated body and includes a proximal end with a second driving feature and a distal end with a setscrew attachment feature.

In other features, rotation of the second cannulated body positions the third cannulated body to reduce the fixation rod within at least one of the screw extender and the spinal implant. The setscrew attachment feature retains a setscrew rotates to engage the setscrew with the spinal implant for securing the fixation rod within the spinal implant. The rod pusher includes a pair of cantilevered arms extending distally away from the third cannulated body. The first driving feature attaches to a removable handle for rotating the second cannulated body. The first cannulated body couples with the screw extender by a threaded connection. The rod pusher includes a ridge for engagement with a slot within the screw extender. The rod pusher includes a curved engagement surface configured to engage a curved surface of the fixation rod.

In still other features, the instrument includes a quick connect sleeve for coupling the first cannulated body with the screw extender. The instrument includes a handle including a first actuation feature that engages the first driving feature and a second actuation feature that engages the second driving feature.

A method for reducing a fixation rod within a screw extender that attaches to a spinal implant includes the steps of coupling a proximal end of a first cannulated body with the screw extender; rotating a second cannulated body within the first cannulated body, the second cannulated body including a proximal end with a first driving feature and a distal end with an internal threaded portion; engaging proximal end of a third cannulated body with the internal threaded portion; engaging a rod pusher on a distal end of the third cannulated body with the fixation rod; and rotating an inserter shaft within the third cannulated body, the inserter shaft including a proximal end with a second driving feature and a distal end with a setscrew attachment feature.

In other features, rotating the second cannulated body positions the third cannulated body to reduce the fixation rod within at least one of the screw extender and the spinal implant.

In still other features, the method includes the steps of retaining a setscrew on the setscrew attachment feature and engaging the setscrew with the spinal implant for securing the fixation rod within the spinal implant; engaging the fixation rod with a pair of cantilevered arms extending distally away from the third cannulated body; attaching a removable handle to the first driving feature and rotating the second cannulated body; coupling the first cannulated body with the screw extender by a threaded connection; engaging a ridge of the rod pusher with a slot within the screw extender; engaging a curved engagement surface of the rod pusher with a curved surface of the fixation rod; coupling the first cannulated body with the screw extender with a quick connect sleeve; and engaging a first actuation feature of a handle with the first driving feature and a second actuation feature of the handle with the second driving feature.

BRIEF DESCRIPTION OF THE DRAWINGS

FIGS. 1A and 1B are perspective views of a first exemplary instrument for reducing and securing spinal rods according to the principles of the present disclosure.

FIGS. 7A and 7B are cross-sectional views of the instrument of FIGS. 6A and 6B along planes VII-A and VII-B according to the principles of the present disclosure.

FIGS. 9A and 9B are side and cross-sectional views along the plane IX-B of the handle of FIG. 8 according to the principles of the present disclosure.

DETAILED DESCRIPTION

Each of the instruments and methods for reducing and securing a spinal rod of the present disclosure includes features that provide a decreased footprint for insertion within the cannula of a screw extender. Each of the instruments includes features for preloading and insertion of a setscrew to secure the spinal rod within the head of a previously inserted screw. Each of the instruments includes features for easy and quick attachment to the screw extender and features various driver attachments for reducing and/or advancing the setscrew to rigidly secure the fixation rod within the head of the screw.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 2:
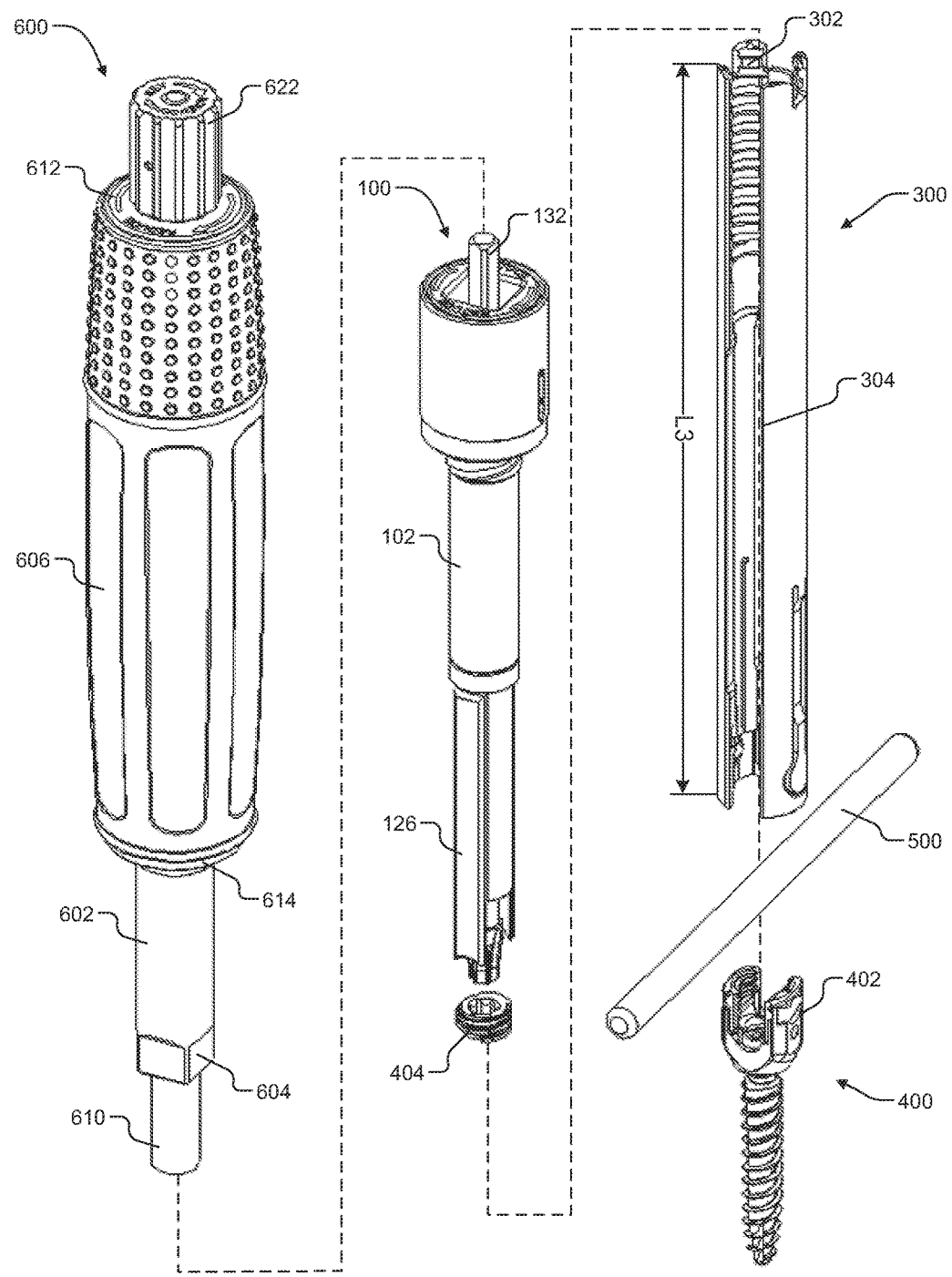
FIG. 2 is an exploded view of a screw extender system, the first exemplar instrument, and a handle according to the principles of the present disclosure.
Figure 3:
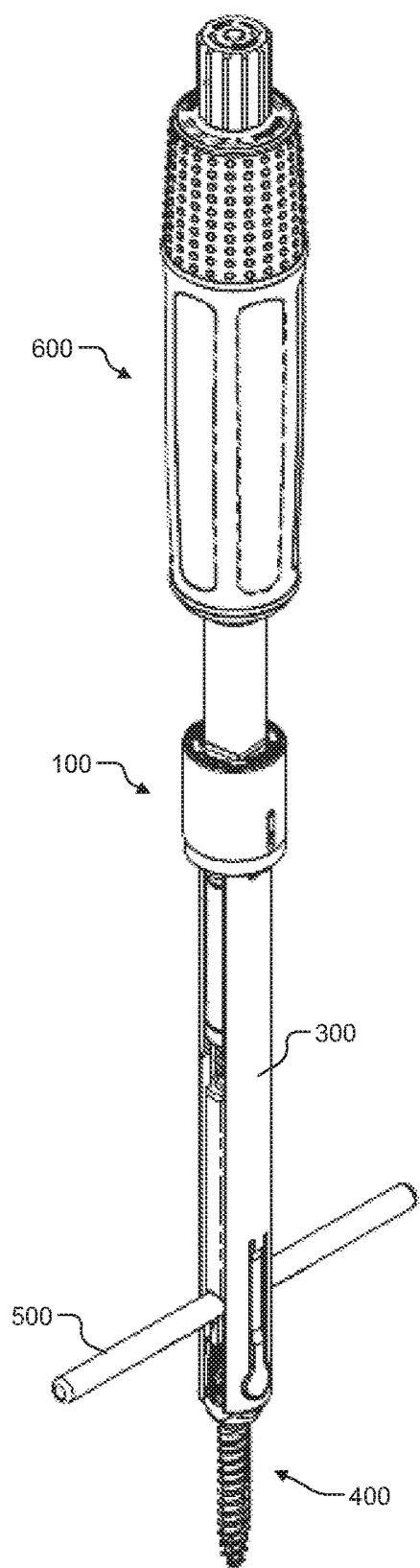
FIG. 3 a perspective view of the instrument and handle engaged with the screw extender system to reduce and secure a spinal rod according to the principles of the present disclosure.

FIGS. 1A and 1B illustrate perspective views of a first exemplary instrument 100 for reducing a fixation rod within a receiving portion of the screw head and inserting a setscrew to rigidly secure the rod to the head. For example, as illustrated in FIGS. 2 and 3, the instrument 100 may be used with a minimally invasive surgery (MIS) system comprising one or more screw extenders 300, screw assemblies 400, and fixation rods 500. Exemplary MIS systems with similar screws, extenders, and rods may be found in commonly assigned U.S. Pub. No. 2010/0036443. However, features of the instrument 100 may be compatible with various other MIS systems known in the art. The instrument 100 may be used with actuation means such as a handle 600 that connects with the instrument 100.

The instrument 100 includes various features to reduce the fixation rod 500 into a receiving portion 402 of the screw assembly 400 and insert a setscrew 404 to retain the fixation rod 500 therein. As illustrated in FIG. 3, the instrument 100 may be inserted into the screw extender 300 and couple at its proximal end. A distal end of the screw extender 300 couples with the receiving portion 402 of the screw assembly 400. The handle 600 attaches to the proximal end of the instrument 100 and includes features to actuate the instrument 100. The fixation rod 500 may be inserted into the distal end of the screw extender 300 while the instrument 100 is in the retracted position. The fixation rod 500 may be advanced distally as the instrument 100 moves towards the extended position. The fixation rod 500 may be fully seated within the receiving portion 402 of the screw assembly 400 when the instrument 100 is in the extended position. Once the fixation rod 500 is fully seated, the handle 600 may include a second actuating feature 604 for actuating the instrument 100 to advance the setscrew 404 into the receiving portion 402 of the screw assembly 400 to rigidly couple the fixation rod 500 therein.

Figure 4:
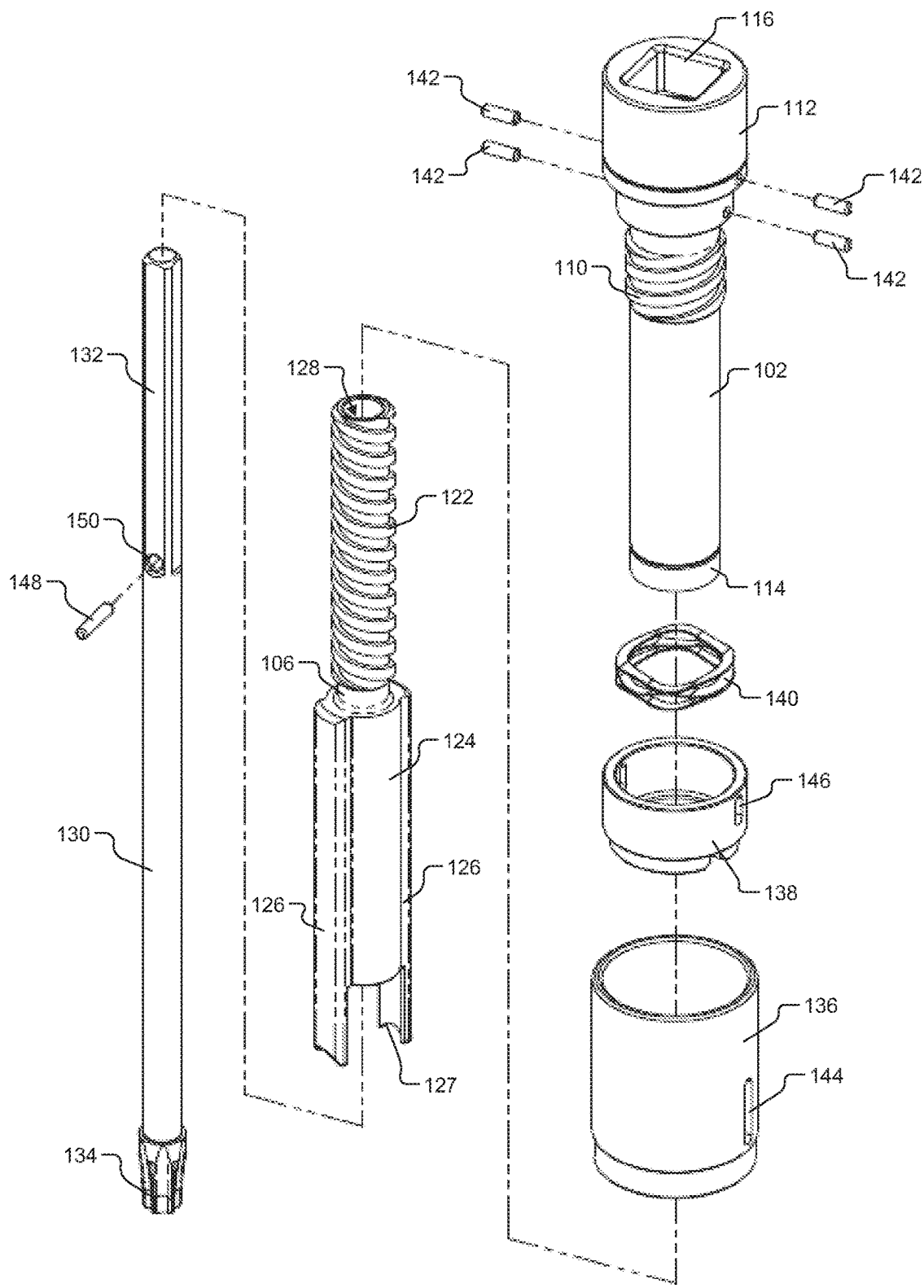
FIG. 4 is an exploded view of the first exemplary instrument according to the principles of the present disclosure.
Figure 5:
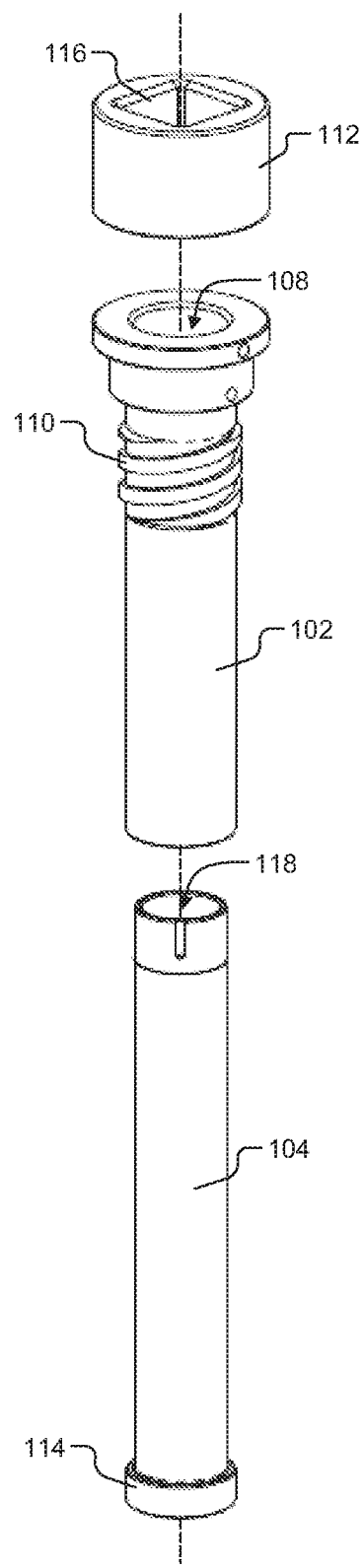
FIG. 5 is an exploded view of first and second cannulated bodies of the first exemplary instrument according to the principles of the present disclosure.
Figure 6A:
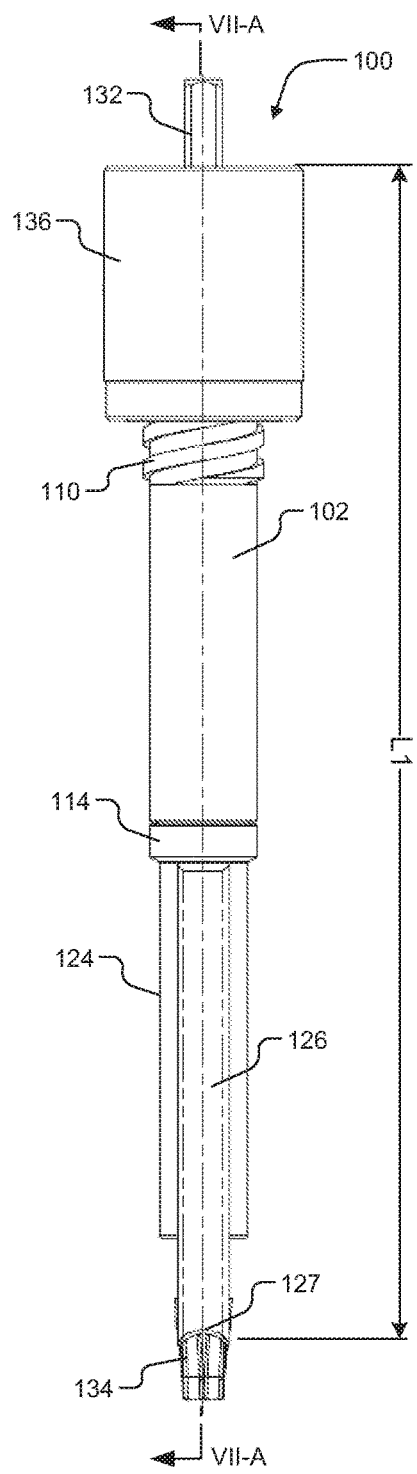
FIGS. 6A and 6B are side views of the first exemplary instrument in a retracted position prior to a reduction step and during the reduction step according to the principles of the present disclosure.
Figure 6B:
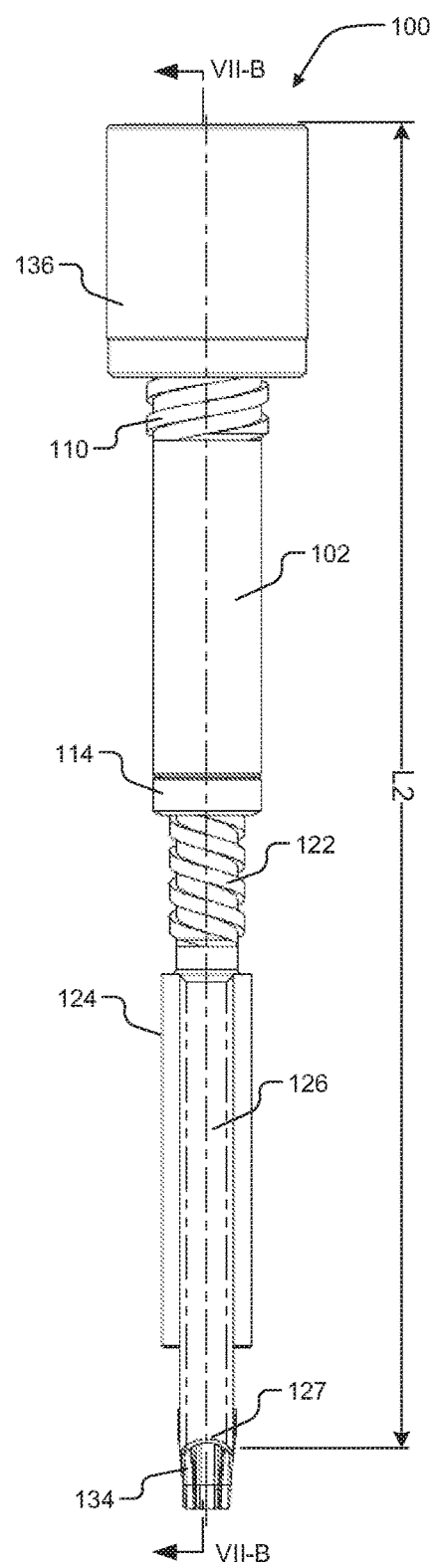

Continuing now also with FIGS. 4 and 5, the instrument 100 may include a plurality of concentric bodies and shafts that rotate relative to one another to linearly displace features that apply force on the fixation rod 500. Various features may engage the screw extender 300 and retain and drive the setscrew 404 to lock the fixation rod 500 with the screw assembly 400. The instrument 100 includes a first body 102, a second body 104, and a third body 106. The first body 102 includes first cannula 108 that receives the second body 104. The first cannula 108 may be substantially smooth from a proximal end to a distal end of the first body 102 which permits rotation of the second body 104 therein. At the proximal end of the first body 102, coupling means, such as an external thread 110, may be configured to couple with mating threads 302 on a proximal end of a screw extender 300 as shown in FIG. 2.

The second body 104 extends through the first cannula 108 and may include retaining portions, such as a proximal cap 112 and a distal lip 114 that extend outside the first cannula 108 and retain the second body 104 therein. The proximal cap 112 and distal lip 114 may retain the second body 104 within the first body 102 while permitting rotation within the first cannula 108. The proximal cap 112 may removably couple with the second body 104 to retain the second body 104 within the first cannula 108. The proximal cap 112 may include a first driving feature 116 that mates with features of the handle 600 for rotating the second body 104 within the first body 102. For example, first driving feature 116 may include a recessed portion including a first geometry such as a rectangular or square shape that mates with corresponding geometry of a first actuating shaft 602 of the handle 600. As the first driving feature 116 is rotated, one or more portions of the second body 104 may rotate in the same direction.

The second body 104 includes a second cannula 118 that receives the third body 106. At a distal end of the second cannula 118, an internally threaded portion 120 may be configured to engage features of the third body 106 as illustrated in detail with FIGS. 7A and 7B. The third body 106 includes a proximal end that engages the internally threaded portion 120 of the second cannula 118. For example, the proximal end may include a mating external threaded portion 122 for threaded engagement with the second cannula 118. The third body 106 includes a distal end that engages the fixation rod 500 as described herein. For example, the distal end may include a rod pusher 124 for engaging the fixation rod 500. The rod pusher 124 includes a substantially cylindrical profile. The rod pusher 124 may include one or more arms 126 extending distally away from the third body 106. For example, the arms 126 may cantilever away from the sides of the rod pusher 124. The arms 126 may terminate in contoured tips 127 conforming to the radius of the fixation rod 500.

The third body 106 may include a third cannula 128 for receiving an inserter shaft 130. The inserter shaft 130 may include features for retaining, inserting, and driving the setscrew 404. In the present example, the inserter shaft 130 includes an elongated, cylindrical profile extending from a proximal end to a distal end. The inserter shaft 130 may rotate freely within the third cannula 128. The proximal end of the inserter shaft 130 may extend proximally through the second cannula 118 and past the first driving feature 116. The proximal end of the inserter shaft 130 may include a second driving feature 132 that mates with an actuator for rotating the inserter shaft 130 within the third body 106. For example, the second driving feature 132 may include a shaped portion of the inserter shaft 130 including a second geometry such as a rectangular or square shape. As the second driving feature 132 is rotated, the inserter shaft 130 may rotate in the same direction. The distal end of the inserter shaft 130 may extend outside the third cannula 128 and include an attachment feature 134 such as a hexalobe or splined pattern. The attachment feature 134 may retain the setscrew 404 by frictional engagement with a recessed portion of the setscrew 404 as known in the art.

Other features of the instrument 100 may include a coupler for quick connect and secure coupling of the instrument 100 to the screw extender 300. The coupler may include an outer sleeve 136, an inner sleeve 138, and a bias mechanism 140. Pins 142 extending radially from the proximal end of the first body 102 may pass through slots 144 in the outer sleeve 136 and slots 146 in the inner sleeve 138 and permit the coupler to slide relative to the first body 102. The bias mechanism 140 may bias the sleeves 136 and 138 distally or proximally. To attach the instrument 100 to the screw extender 300, the user may compress or expand the bias mechanism 140 to engage the external thread 110 on the first body 102 with the mating threads 302 of the screw extender 300. In other features, a limit pin 148 may extend through a transverse slot 150 in the inserter shaft 130. The limit pin 148 may limit advancement of the inserter shaft 130 distally through the third cannula 128 by engagement with the proximal end of the third body 106. For example, ends of the limit pin 148 may extend outside the transverse slot 150 to engage the distal end of the third body 106 as the inserter shaft 130 slides distally through the third cannula 128. Thus, the inserter shaft 130 may rotate freely in the third cannula 128 but not pass completely through the third cannula 128.

FIGS. 6A-7B illustrate additional views of the instrument 100 in both retracted (FIGS. 6A and 7A) and extended (FIGS. 6B and 7B) positions as used with MIS systems. In the retracted position, the instrument 100 includes a first overall length L1 as measured from a top surface of the proximal cap 112 to the contoured tips 127 of the arms 126. As the second body 104 rotates, the external threaded portion 122 of the rod pusher 124 engages the internally threaded portion 120 of the second cannula 118. Rotation in a first direction, such as a clockwise direction, causes the rod pusher 124 to extend distally. Rotation in a second direction, such as a counter-clockwise direction, causes the rod pusher 124 to retract proximally. In the extended position, the instrument includes a second overall length L2 as measured from the top surface of the proximal cap 112 to the contoured tips 127 of the arms 126. The second length L2 may be greater than the first length L1. Both the first length L1 and the second length L2 may be less than a length L3 of the screw extender 300 as shown in FIG. 2. The inserter shaft 130 may freely float within the third cannula 128 as the rod pusher 124 retracts and extends relative to the second body 104. The limit pin 148 limits movement of the inserter shaft 130 distally by engaging the upper surface of the rod pusher 124.

Figure 8:
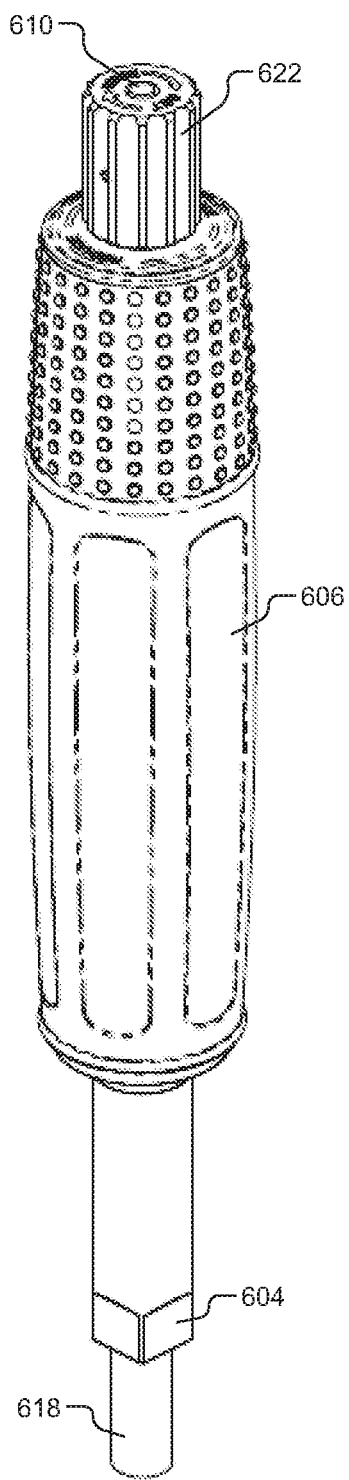
FIG. 8 is a perspective view of the handle according to the principles of the present disclosure.

FIGS. 8-9B illustrate additional features of the handle 600 for actuation of the instrument 100. The handle 600 includes a handle body 606 with the second actuating feature 604 at its distal end. The second actuating feature 604 may engage the first driving feature 116 of the instrument 100. For example, the second actuating feature 604 may include a shaped portion of the handle body 606 corresponding to the shape of the first driving feature 116, such as a square or rectangular profile. The handle body 606 may include an outer gripping surface such as applied silicone. As the handle body 606 rotates, the second actuation feature 604 rotates. The handle body 606 may include a fourth cannula 608 through which a handle shaft 610 extends. The fourth cannula 608 may extend from a proximal end to a distal end of the handle 600.

A proximal cap 612 and a distal cap 614 may thread onto the ends of the fourth cannula 608 and include apertures through which the handle shaft 610 may pass. The apertures 616 may provide bearing surfaces for improved rotation of the handle shaft 610 within the handle body 606. A third actuating feature 618 on the distal end of the handle shaft 610 may extend outside the fourth cannula 608. The third actuating feature 618 may engage the second driving feature 132 of the instrument 100. For example, the third actuating feature 618 may include a recessed portion 620 or pocket corresponding to the shape of the second driving feature 132, such as a square or rectangular profile. On the proximal end of the handle shaft 610, a knob 622 may be used to rotate the handle shaft 610.

Referring now to FIGS. 10A-12B, the instrument 100 is shown coupled within the screw extender 300 that is attached to the screw assembly 400. The instrument 100 may be actuated by the handle 600 to reduce the fixation rod 500 within the screw assembly 400 and insert the setscrew 404 to retain the fixation rod 500 within the receiving portion 402. For example, the proximal end of the instrument 100 may be coupled to the proximal end of the screw extender 300 via threaded engagement and/or the coupler sleeves 136 and 138. The first body 102, second body 104, and third body 106 extend distally into the screw extender 300.

Figure 10A:
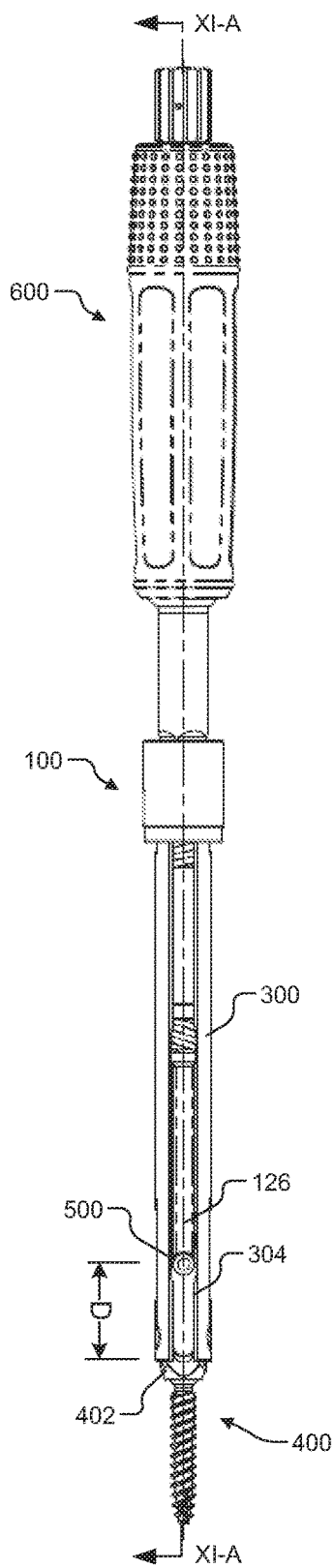
FIGS. 10A and 10B are side views of the first exemplary instrument reducing the fixation rod within the screw extender system according to the principles of the present disclosure.
Figure 11A:
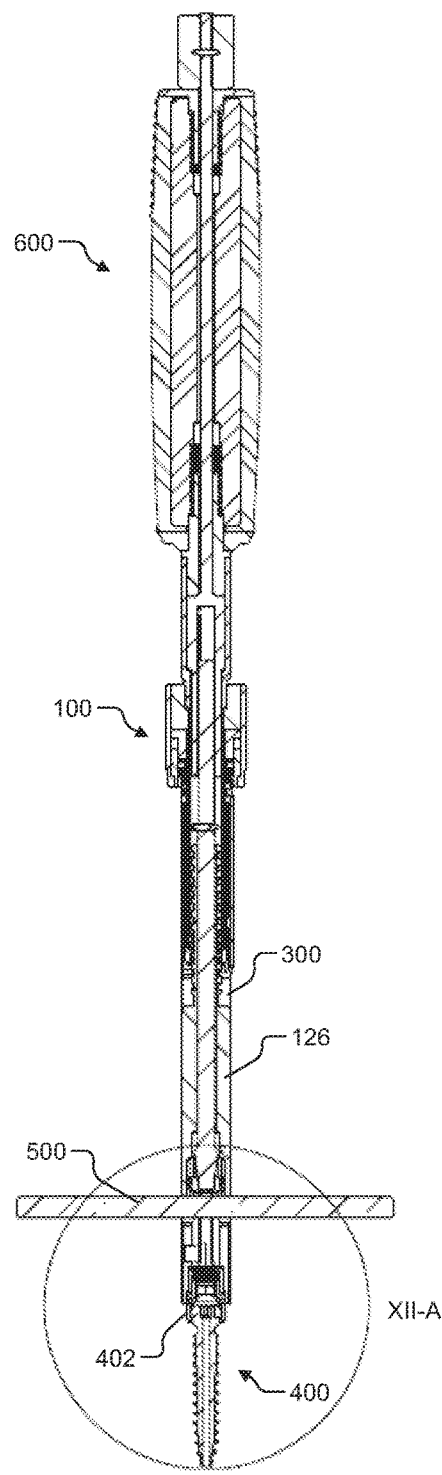
FIGS. 11A and 11B are cross-sectional views of the instrument of FIGS. 10A and 10B along the planes XI-A and XI-B respectively according to the principles of the present disclosure.
Figure 12A:
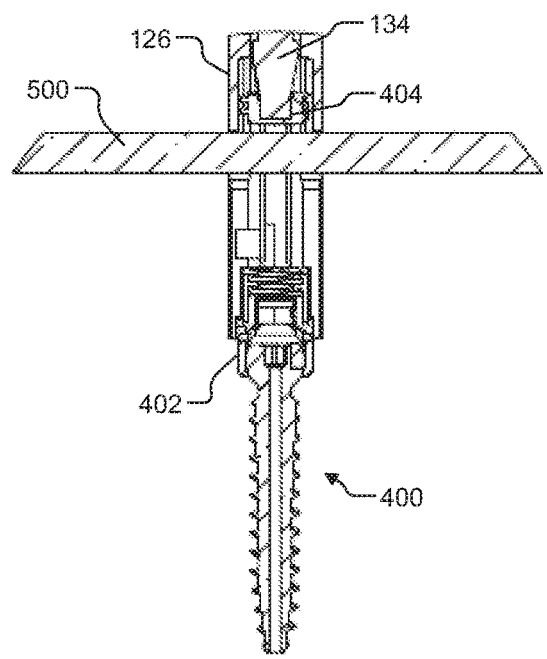
FIGS. 12A and 12B are enlarged views of the instrument of FIGS. 11A and 11B in circled areas XII-A and XII-B respectively according to the principles of the present disclosure.

In the retracted position as best illustrated in FIGS. 10A, 11A, and 12A, the contoured tips 127 of the arms 126 may begin to engage the fixation rod 500 at some distance from the receiving portion 402 of the screw assembly 400. The setscrew 404 may be secured to the attachment feature 134 of the inserter shaft 130 which floats freely within the third cannula 128. As the handle body 606 rotates in the first direction, the second actuating feature 604 rotates second body 104 within the first body 102 via the first driving feature 116. The rotational movement causes the rod pusher 124 to advance distally and apply force to the fixation rod 500 via the arms 126. The inserter shaft 130 may follow the rod pusher 124 distally with the attached setscrew 4040 floating just above the fixation rod 500. The rod pusher 124 continues to advance distally until the fixation rod 500 is seated within the receiving portion 402 of the screw assembly 400.

Figure 10B:
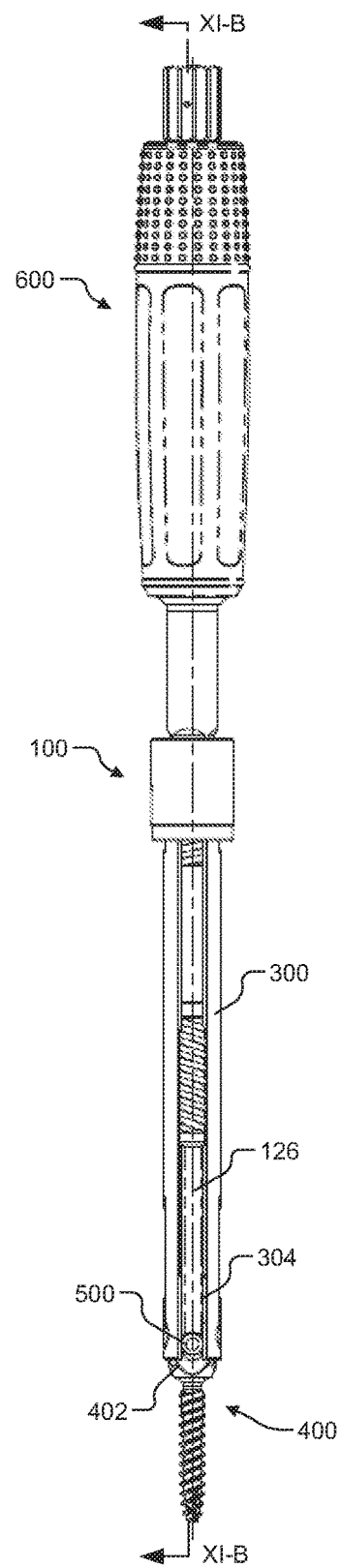
Figure 11B:
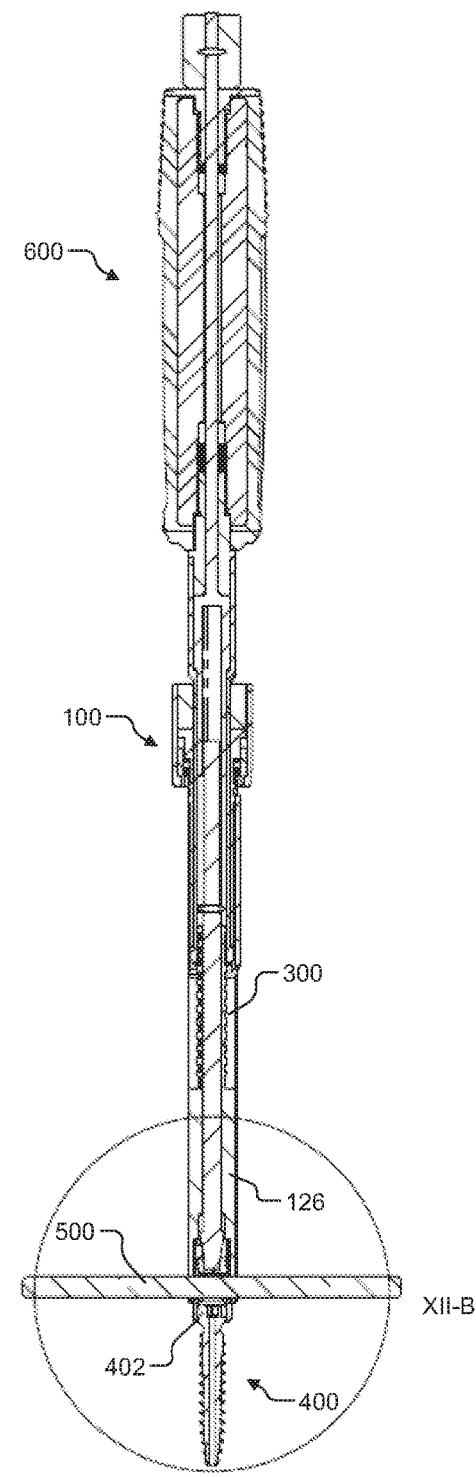
Figure 12B:
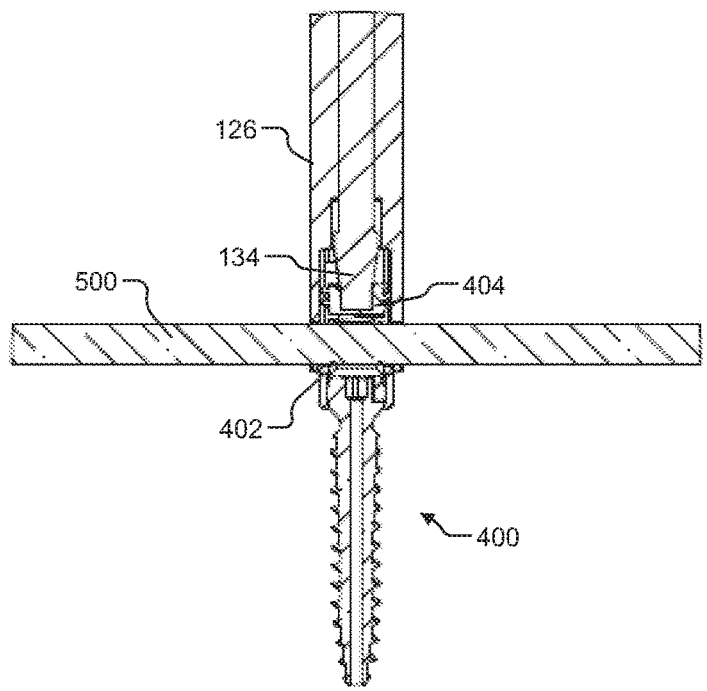

In the extended position as best illustrated in FIGS. 10B, 11B, and 12B, the contoured tips 127 of the arms 126 may continue to engage the fixation rod 500 and hold it within the receiving portion 402 of the screw assembly 400. The setscrew 404 may be advanced by the inserter shaft 130 onto threads of the receiving portion 402 by rotating the knob 622 of the handle 600. As the knob 622 rotates in a first direction, for example a clockwise direction, the setscrew 404 may engage more of the thread of the receiving portion 402 and advance distally towards the fixation rod 500. The knob 622 may rotate in a second opposite direction, for example, a counter-clockwise direction, to remove the setscrew 404. Once the setscrew 404 has been inserted and tightened sufficiently, the instrument 100 may be uncoupled from the screw extender 300.

Figure 13A:
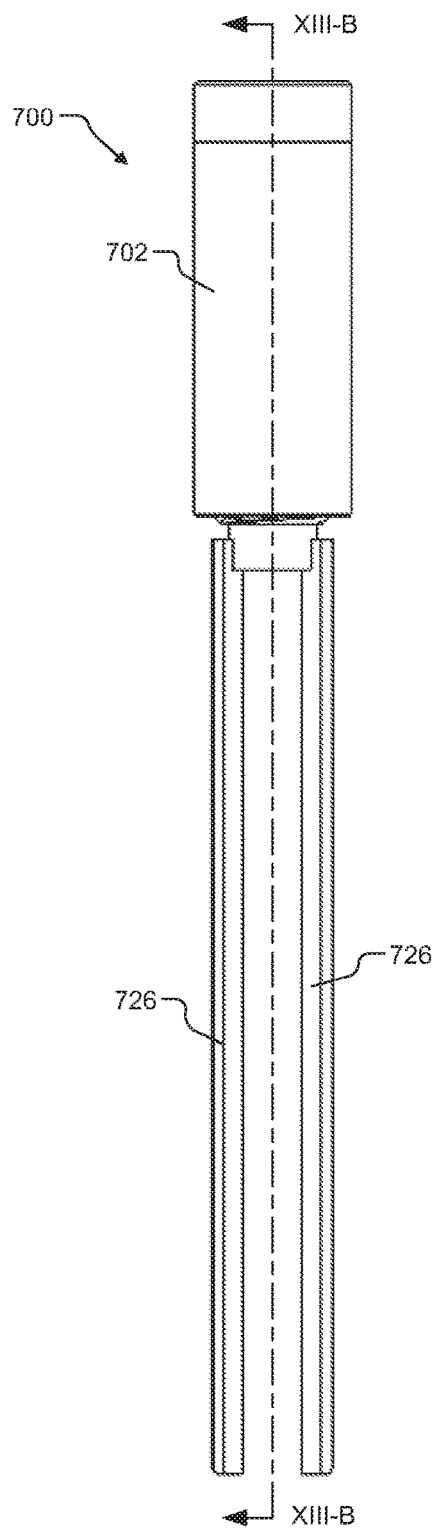
FIGS. 13A and 13B are side and cross-sectional views along the plane XIII-B of a second exemplary instrument for reducing the fixation rod within a screw extender system according to the principles of the present disclosure.
Figure 13B:
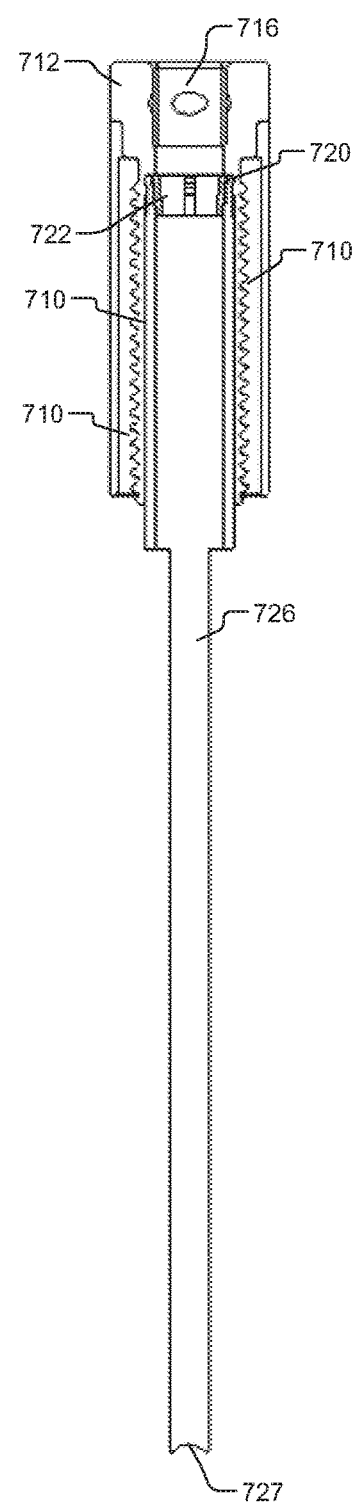
Figure 14:
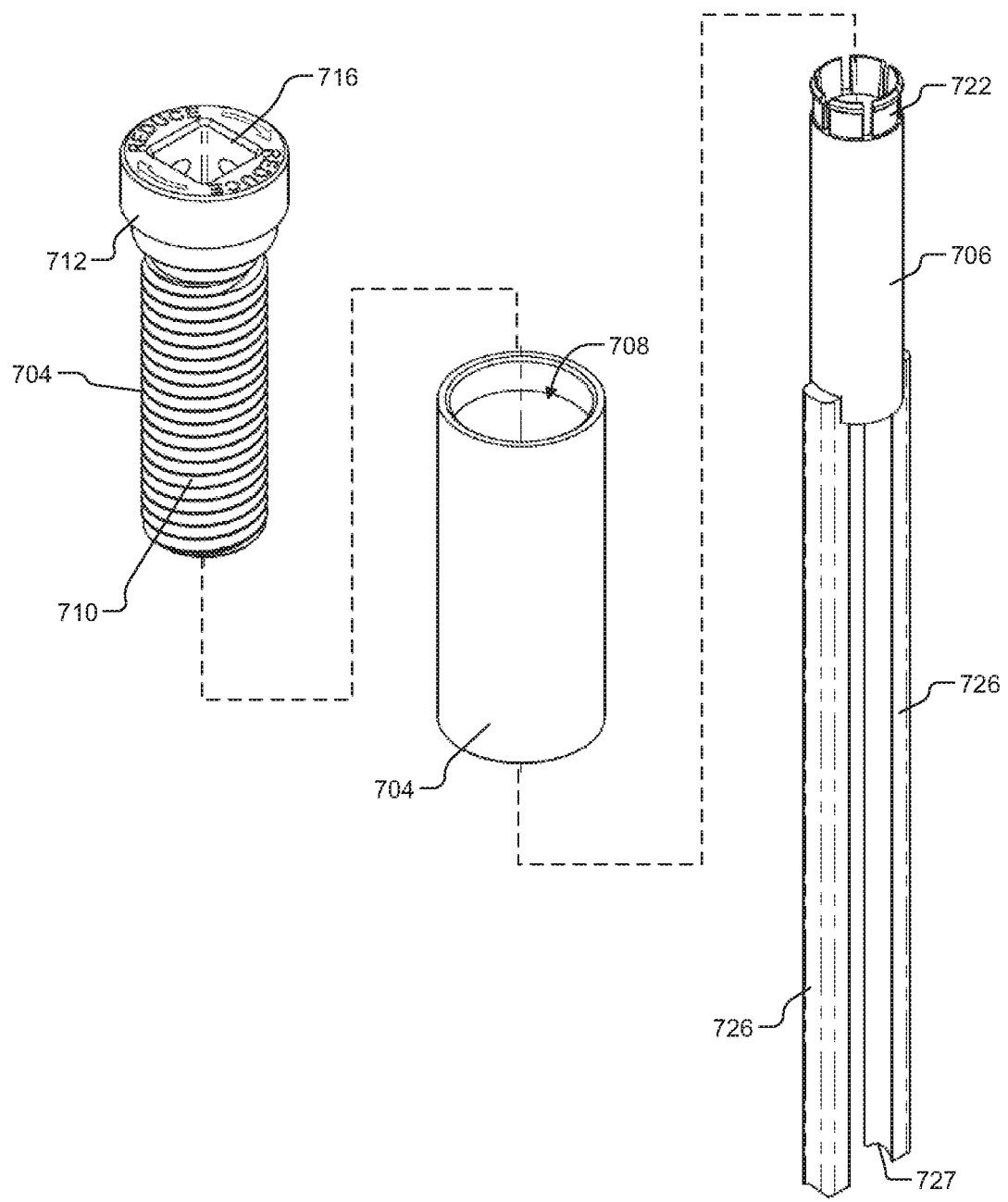
FIG. 14 is an exploded view of the instrument of FIGS. 13A and 13B according to the principles of the present disclosure.

FIGS. 13A-14 illustrate another exemplary instrument 700 for reducing a fixation rod within a screw extender. The instrument 700 includes a first body 702, a second body 704, and a third body 706. The first body 702 includes a first cannula 708 that receives the second body 704. The first cannula 708 may be substantially smooth from a proximal end to a distal end of the first body 702 to permit rotation of the second body 704 therein. The first body 702 may slide over the proximal end of a screw extender such as screw extender 300. The second body 704 may include a threaded portion 710 for engagement with the mating threads 302 of the screw extender 300. A proximal end of the second body 704 may include a proximal cap 712 with a driving feature 716. The driving feature 716 mates with features of the handle 600 for rotating the second body 704 within the first body 702. For example, driving feature 716 may include a recessed portion including a first geometry such as a rectangular or square shape that mates with corresponding geometry of the first actuating shaft 602 of the handle 600. As the driving feature 716 is rotated, one or more portions of the second body 704 may rotate in the same direction.

The second body 704 includes a second cannula 718 that receives the third body 706. The third body 706 includes a proximal end that engages the second cannula 718. For example, the proximal end may include a flexible collet 720 for engagement with one or more grooves 722 within the second cannula 718. The flexible collet 720 may snap into the groove 722 by elastically deforming radially inward. Once the flexible collet 720 couples within the groove 722, the third body 706 may rotate within the second cannula 718. The third body 706 includes a distal end that engages the fixation rod 500 as described herein. For example, the distal end may include a rod pusher 724 for engaging the fixation rod 500. The rod pusher 724 includes a substantially cylindrical profile. The rod pusher 724 may include one or more arms 726 extending distally away from the third body 706. For example, the arms 726 may cantilever away from the sides of the rod pusher 724. The arms 726 may terminate in contoured tips 727 conforming to the radius of the fixation rod 500.

The present exemplary instrument 700 may reduce the fixation rod 500 within the screw assembly 400 by threaded engagement with mating threads 302 on the screw extender 300. For example, the instrument 700 may be threaded onto the screw extender by engaging threaded portion 710 with the mating threads 302. The arms 726 may engage the slots 304 of the screw extender 300. The handle 600 or other actuation instrument may be inserted into the driving feature 716 to rotate the second body 704 to either advance the instrument 700 distally or proximally within the screw extender 300. For example, rotating the second body 704 in a first direction, such as a clockwise direction, advances the instrument 700 distally to engage the arms 726 with the fixation rod 500 for reduction. Rotating the second body 704 in a second direction, such as a counter-clockwise direction, retracts the instrument 700 proximally to disengage the arms 726. The third body 706 may include a third cannula 728 to receive an inserter shaft similar to the inserter shaft 130 of the instrument 100 of FIGS. 1-12.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A method for reducing a fixation rod within a screw extender that attaches to a spinal implant, comprising:
    coupling a proximal end of a first cannulated body with the screw extender;
    rotating a second cannulated body within the first cannulated body, the second cannulated body including a first driving feature;
    actuating a rod pusher with the first driving feature so as to engage the rod pusher with the fixation rod, the rod pusher having a bore and a pair of cantilever arms extending distally therefrom; and
    rotating an inserter shaft within the first cannulated body, second cannulated body and bore of the rod pusher, the inserter shaft including a proximal end with a second driving feature and a distal end with a setscrew attachment feature for engaging a setscrew.

2. The method of claim 1, wherein rotating the second cannulated body positions the rod pusher to reduce the fixation rod within at least one of the screw extender and the spinal implant.

3. The method of claim 1, further comprising retaining a setscrew on the setscrew attachment feature of the inserter shaft and engaging the setscrew with the spinal implant for securing the fixation rod within the spinal implant.

4. The method of claim 1, wherein the pair of cantilever arms terminate in contoured tips.

5. The method of claim 4, wherein the contoured tips conform to the radius of the fixation rod.

6. The method of claim 1, further comprising attaching a removable handle to the first driving feature and rotating the second cannulated body.

7. The method of claim 1, further comprising coupling the first cannulated body with the screw extender by a threaded connection.

8. The method of claim 1, further comprising engaging a ridge of the rod pusher with a slot within the screw extender.

9. The method of claim 1, further comprising engaging a curved engagement surface of the rod pusher with a curved surface of the fixation rod.

10. The method of claim 1, further comprising coupling the first cannulated body with the screw extender with a quick connect sleeve.

11. The method of claim 1, further comprising engaging a first actuation feature of a handle with the first driving feature of the second cannulated body and a second actuation feature of the handle with the second driving feature of the inserter shaft.

12. The method of claim 1, further comprising the step of providing a third cannulated body, the third cannulated body disposed on the proximal end of the rod pusher, wherein the distal end of the second cannulated body includes an internal threaded portion and engaging the proximal end of the third cannulated body with the internal threaded portion so as to actuate the rod pusher.

* * * * *